US00PP30424P2

(12) United States Plant Patent
Cain

(10) Patent No.: US PP30,424 P2
(45) Date of Patent: Apr. 23, 2019

(54) GRAPEVINE NAMED 'IFG THIRTY'

(50) Latin Name: ***Vitis interspecific* hybrid**
Varietal Denomination: IFG Thirty

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/732,230

(22) Filed: Oct. 10, 2017

(51) Int. Cl.
*A01H 5/08* (2018.01)

(52) U.S. Cl.
USPC ..... Plt./205

(58) Field of Classification Search
USPC ..... Plt./205
CPC ..... A01H 5/0812; A01H 5/08; A01H 5/00; A01H 5/02; A01H 6/88
See application file for complete search history.

(56) References Cited

U.S. PATENT DOCUMENTS

PP25,434 P3 4/2015 Cain

OTHER PUBLICATIONS

Upov International Union for the Protection of New Varieties of Plants Grapevine Guidelines for the Conduct of Tests for Distinctness, Uniformity and Stability TG/50/9, 2008 pp. 1-5. (Year: 2008).*

* cited by examiner

*Primary Examiner* — June Hwu

(57) ABSTRACT

This invention is a new and distinct grapevine variety denominated 'IFG Thirty'. The new grapevine 'IFG Thirty' is characterized by producing naturally large, ovate to elongated ovate, black seedless berries which are firm in texture, medium low in acidity and ripen late in the growing season.

1 Drawing Sheet

Latin name of the genus and species claimed: *Vitis interspecific* hybrid.

Variety denomination: 'IFG Thirty'.

BACKGROUND OF THE INVENTION

The new and distinct grapevine described and claimed herein originated from a hand pollination of the 06095-096-043, an unnamed interspecific seedling selection from the IFG breeding program, and 'IFG Sixteen' (U.S. Plant Pat. No. 25,434) hybridized in May 2009. The abortive seed traces were subsequently embryo cultured and the resulting 47 plants were planted in the field in April 2010. The present variety of grapevine was selected as a single plant in September 2012 and was first asexually propagated by hardwood cuttings in December 2012 near Delano, Kern County, Calif. These resulting cuttings produced second generation plants that were planted during April 2013 at the International Fruit Genetics LLC research facility near Delano, Kern County, Calif. and were observed for four years and found to be true-to-type.

BRIEF SUMMARY OF THE INVENTION

The new grapevine 'IFG Thirty' is characterized by producing naturally large, ovate to elongated ovate, black seedless berries which are firm in texture, medium low in acidity and ripen late in the growing season. Fruits normally ripen late August to mid-September near Delano, Calif.

To the inventor's knowledge, the new grapevine variety is most similar to the 'Autumn Royal' variety. 'IFG Thirty' can be distinguished from the Autumn Royal variety by having a broader, more desirable cluster shape and thicker and tougher peduncle and pedicle, by having a much smaller residual seed trace, by having no tendency to develop an astringent flavor and by having higher, more consistent yields.

'IFG Thirty' can be distinguished from its female parent, the IFG 06095-096-043, by having larger, more elongated berries which are more fully black in color and by having larger clusters. 'IFG Thirty' can be distinguished from its pollen parent, the 'IFG Sixteen', by having firmer berries that more easily attain full black color under hot conditions and by ripening slightly earlier.

BRIEF DESCRIPTION OF THE DRAWING

The accompanying photographic drawing in FIG. 1 illustrates in full color 'IFG Thirty', taken from a 4-year-old vine. The photograph was taken outdoors with indirect lighting. The colors are as nearly true as is reasonably possible in a color representation of this type. The top portion of the drawing has a mature leaf. A mature fruit cluster is represented in the center of the drawing along with a typical berry in cross section. A young shoot tip with tendrils and young leaves can be seen on the bottom portion of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Thirty' plants grown in the vicinity of Delano, Kern County, Calif. during 2015, and is believed to apply to plants of the variety grown under similar conditions of soil and climate elsewhere:

Vine:

*General*.—Vigor — Moderate. Density of foliage — Medium. Productivity — Very productive, produces about 45 to 68 kg of fruit per vine. Root stock — Own root. Training method — Typically spur pruned leaving 2 bud spurs.

*Trunk*.—Trunk diameter of 4-year-old vines at 30 cm above the soil line — About 4.5 cm. Shape — Medium to slightly stocky. Straps — Long, continuous. Surface texture — Slightly shaggy. Inner bark color — The following colors were observed: Greyed-orange: 177A and 166A.

Shoots:

*Young shoot*.—Form of tip — Wide open. Distribution of anthocyanin coloration of tip — Absent. Density of prostrate hairs of tip — Sparse. Density of erect hairs of tip — Sparse. Color — Yellow-green: 144A.

*Woody shoot* (*mature canes*).—Shape — Medium to somewhat stocky. Internode length — Medium: about 12.2 cm. Width at node — About 1.3 cm. Cross section — Circular. Surface — Striate. Main color — The following colors were observed: Greyed-orange: 177A and 177B and 175A. Density of erect hairs of nodes — None or very sparse. Density of erect hairs on internodes — None or very sparse. Axillary shoot length at full bloom — Weak to medium, approximately 5.7 cm.

*Flowering shoot*.—Vigor during flowering — Medium. Attitude during flowering on shoots not tied — Semi-erect. Color — dorsal side of internodes — Yellow-green: 146C, with Red-purple stripes: 59B. Color — ventral side of internodes — Yellow-green: 146C. Color — dorsal side of nodes — Yellow-green: 146C. Color — ventral side of nodes — Yellow-green: 146C. Density of prostrate hairs on nodes — Sparse. Density of erect hairs on nodes — None. Density of prostrate hairs on internode — Very sparse. Density of erect hairs on internode — None. Anthocyanin coloration of buds — Absent.

*Tendrils*.—Distribution on the shoot (at full flowering) — Discontinuous. Length of tendril — Long: about 29.6 cm. Thickness of tendril 2 cm from base — About 2.9 cm. Color — Yellow-green: N144A. Form — Bifurcated and trifurcated. Number of consecutive tendrils — 2.

Leaves

*Young leaves*.—Color of upper surface of first four distal unfolded leaves — Yellow-green: 144A. Average intensity of anthocyanin coloration of six distal leaves prior to flowering — Very weak. Density of prostrate hairs between veins (lower surface) — Very sparse. Density of prostrate hairs on veins (lower surface) — Sparse to medium. Density of erect hairs between veins (lower surface) — Absent. Density of erect hairs on veins (lower surface) — Sparse.

*Mature leaves*.—Average length — About 16.5 cm. Average width — About 22.8 cm. Mature leaf size — Large. Shape of blade — Wedge-shaped. Number of lobes — 5. Blade venation — Palmate. Anthocyanin coloration of main veins on upper side of blade — Very weak. Mature leaf profile — Flat. Blistering surface of blade upper surface — Very weak. Leaf apex — Acute. Undulation of margin — Slight. Thickness — Medium. Undulation of blade between main and lateral veins — Slight undulation over entire area. Shape of teeth — Both sides concave. Length of teeth — Medium. Ratio length/width of teeth — Medium. Shape of upper lateral sinuses — Open to lobes slightly overlapping. Depth of upper lateral sinuses — Medium. General shape petiole sinus — Wide open. Shape of base of upper leaf sinuses — V-shaped. Tooth at petiole sinus — Absent. Density of prostrate hairs between veins on lower surface of blade — Very sparse. Density of erect hairs between veins on lower surface of blade — Absent. Density of prostrate hairs on main veins on lower surface of blade — Very sparse. Density of erect hairs on main veins on lower surface of blade — Sparse. Density of prostrate hairs on main veins on upper surface of blade — Very sparse. Density of erect hairs on main veins on upper surface of blade — None. Autumn coloration of leaves — Leaves can be a single color or combination of colors, in a mottled pattern or on the edges of the leaves: The following colors were observed: Greyed-yellow: 162A and 162B, Greyed-purple: N186B and187A and 187B and 184A, Greyed-red: 181A and 181B and 181C.

*Upper surface*.—Color — The following colors were observed: 137A and 137B and 137C. Color of main veins — Yellow-green: 145A. Anthocyanin coloration of main veins (upper surface) — Very weak: Red-purple: 59B. Surface appearance — Dull. Blistering surface of blade — Very weak.

*Lower surface*.—Color — Yellow-green: 146B. Color of main veins — Yellow-green: 145C. Anthocyanin coloration of main veins (lower surface) — Absent. Glossiness — Weak. Surface texture — Smooth. Surface appearance — Dull.

*Petiole*.—Length — About 13 cm. Diameter of petiole 2 cm from blade — 3.3 mm. Petiole color — The following colors were observed: Yellow-green: 145A and 145B and Red-purple: 59B. Length of petiole compared to middle vein — Slightly shorter. Density of prostrate hairs on petiole — Very sparse. Density of erect hairs on petiole — None.

*Buds*.—Bud fruitfulness — Basal: Mostly fruitful. Position of first fruitful shoot on previous season cane — $1^{st}$ to $2^{nd}$ node. Dormant bud length — About 5.2 mm. Dormant bud width in the proximal/distal plane — About 5.8 mm. Dormant bud color — Greyed-orange: 166A. Time of bud burst — Mid-season: about Mar. 5, 2015.

Flowers:

*General*.—Flower sex — Hermaphrodite. Length of single flower, unopened — About 3.5 mm. Width of single flower — Unopened: About 1.8 mm. Opened: About 7.0 mm. Stamen count — 5. Pollen color — Yellow: 10A. Pistil length — About 3.5 mm. Pistil color — Yellow-green: 144A. Length of first inflorescence — Medium — long: About 18.7 cm long by 14.1 cm wide. Position of first flowering and fruiting node — $3^{rd}$ to $4^{th}$ node (current season growth). Number of inflorescence per flowering shoot — 1.1 to 2. Time of bloom — Medium as compared with similar varieties in the growing area of Delano, Calif. Date of full bloom — About May 2, 2015.

Fruit:

*General*.—Ripening period — Mid to late season: Approximately Aug. 31, 2015. Use — Fresh market. Keeping quality — Good to excellent: remains commercially acceptable when stored up to 8 weeks at 0° C. and high RH. Resistance to — Insects: Average typical of *Vitis vinifera* species. Diseases: Average typical of *Vitis vinifera* species. Refractometer test — Soluble solids: about 17.8. Brix/acid — About 57.4%. % Titratable acidity — About 0.31. Juice pH — About 3.59. Juice color — Greyed-purple: 182B.

*Cluster*.—Mature cluster length (peduncle excluded) — About 26.1 cm. Mature cluster width — About 20.3 cm. Mature cluster weight — About 1516 g. Bunch density — Medium. Number of berries — About 242. Form — Conical.

*Peduncle*.—Lignification of peduncle — Weak. Length of peduncle — Medium, approximately 4.3 cm. Color of peduncle — Yellow-green: 145A.

*Berry*.—Uniformity of size — Uniform. Single berry weight — About 7.3 g natural: to about 7.3 g when treated with gibberellic acid. Shape — Ovate to elongated ovate. Seeds — Absent. Cross section — Circular. Berry dimensions — Longitudinal axis: about 37.0 mm: horizontal axis: about 20.2 mm. Pedicel length — About 9.1 mm. Pedicel width — About 1.4 mm. Pedicel color — Yellow-green: 144C. Berry firmness — Moderately firm. Berry juiciness — Moderately juicy. Particular flavor — Neutral. Bloom (cuticular wax) — Medium. Berry separation from pedicel — Moderate. Skin color (without bloom) — The following colors were observed: Greyed-purple: N186A and N186B. Flesh color — White: 155A. Anthocyanin coloration of flesh — Absent.

*Skin*.—Thickness — Medium. Skin toughness — Not notable when chewing. Reticulation — Absent. Tenacity — Tenacious to flesh.

What is claimed:

1. A new and distinct variety of grapevine as herein illustrated and described.

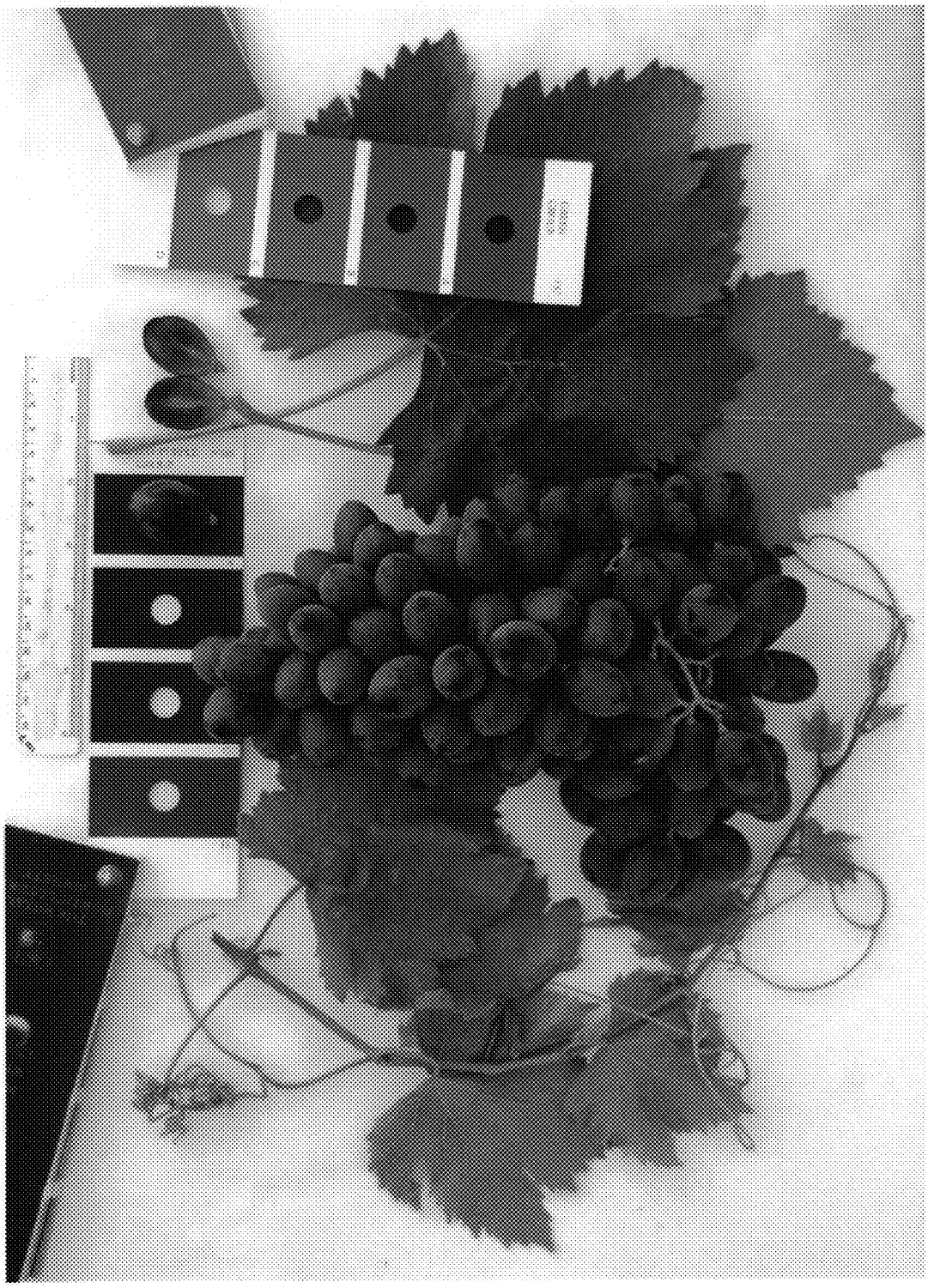

* * * * *